United States Patent
Amin et al.

(10) Patent No.: US 11,828,749 B2
(45) Date of Patent: Nov. 28, 2023

(54) AIRBORNE ORGANIC MATTER DETECTION SYSTEM AND METHOD

(71) Applicant: KING ABDULLAH UNIVERSITY OF SCIENCE AND TECHNOLOGY, Thuwal (SA)

(72) Inventors: Osama Amin, Thuwal (SA); Basem Shihada, Thuwal (SA); Mohamed-Slim Alouini, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 262 days.

(21) Appl. No.: 17/276,594

(22) PCT Filed: Sep. 10, 2019

(86) PCT No.: PCT/IB2019/057613
§ 371 (c)(1),
(2) Date: Mar. 16, 2021

(87) PCT Pub. No.: WO2020/065427
PCT Pub. Date: Apr. 2, 2020

(65) Prior Publication Data
US 2022/0042973 A1 Feb. 10, 2022

Related U.S. Application Data

(60) Provisional application No. 62/736,586, filed on Sep. 26, 2018.

(51) Int. Cl.
*G01N 33/497* (2006.01)
*G07C 9/15* (2020.01)
*G01V 8/12* (2006.01)

(52) U.S. Cl.
CPC .............. *G01N 33/497* (2013.01); *G01V 8/12* (2013.01); *G07C 9/15* (2020.01); *G01N 2033/4975* (2013.01)

(58) Field of Classification Search
CPC ..... G01N 2001/2223; G01N 2001/024; G01N 2001/022; G01N 1/2273; G01N 2001/2276
See application file for complete search history.

(56) References Cited

U.S. PATENT DOCUMENTS 4,045,997 A * 9/1977 Showalter .......... G01N 33/0011
340/632
4,202,200 A * 5/1980 Ellson ..................... G01N 1/26
73/31.05
(Continued)

FOREIGN PATENT DOCUMENTS

JP 2017032246 A 2/2017

OTHER PUBLICATIONS

Arya, S.P., et al., "Air Pollution Meteorology and Dispersion," Chapter 6—Gradient Transport Theories, Oxford University Press New York, 1999, vol. 6, pp. 127-154.
(Continued)

*Primary Examiner* — David A. Rogers
(74) *Attorney, Agent, or Firm* — PATENT PORTFOLIO BUILDERS PLLC

(57) ABSTRACT

An aerosol detection system for detecting airborne organic matter, the detection system including a corridor extending along a longitudinal axis and having first and second ends; an access gate connected to the first end of the corridor and configured to control access of an individual to the corridor; a person detection system located in the corridor and configured to determine the presence of the individual inside the corridor; and a testing set configured to generate an air puff, which directs an exhaled breath of the individual for deter-
(Continued)

mining a presence of the airborne organic matter. The corridor has a width $w_c$ that allows movement of a single individual past the testing set.

20 Claims, 11 Drawing Sheets

(56) References Cited

U.S. PATENT DOCUMENTS

| | | | | |
|---|---|---|---|---|
| 4,586,441 | A * | 5/1986 | Zekich | E05G 5/02 |
| | | | | 109/6 |
| 4,896,547 | A * | 1/1990 | Arney | G01V 9/007 |
| | | | | 73/863.81 |
| 4,909,089 | A * | 3/1990 | Achter | G01N 1/24 |
| | | | | 73/863.11 |
| 4,964,309 | A * | 10/1990 | Jenkins | G01N 1/24 |
| | | | | 73/864.81 |
| D313,766 | S * | 1/1991 | Arney | D10/104.1 |
| 4,987,767 | A * | 1/1991 | Corrigan | G01N 27/622 |
| | | | | 250/282 |
| 5,753,832 | A * | 5/1998 | Bromberg | G01N 1/2205 |
| | | | | 73/864.81 |
| 5,915,268 | A * | 6/1999 | Linker | G01V 9/007 |
| | | | | 73/28.01 |
| 6,073,499 | A * | 6/2000 | Settles | G01V 9/007 |
| | | | | 73/864.81 |
| 6,334,365 | B1 * | 1/2002 | Linker | G01N 1/2214 |
| | | | | 73/864.81 |
| 6,366,203 | B1 * | 4/2002 | Burns | G01V 3/00 |
| | | | | 340/572.1 |
| 6,375,697 | B2 * | 4/2002 | Davies | B08B 5/02 |
| | | | | 96/417 |
| 6,610,977 | B2 * | 8/2003 | Megerle | G01N 1/2202 |
| | | | | 73/28.01 |
| 6,708,572 | B2 * | 3/2004 | Jenkins | G01N 1/2202 |
| | | | | 73/864.33 |
| 6,790,249 | B2 * | 9/2004 | Davies | B08B 5/02 |
| | | | | 55/467 |
| 6,975,227 | B1 * | 12/2005 | Nishikawa | G07C 9/37 |
| | | | | 340/541 |
| 7,136,513 | B2 * | 11/2006 | Waehner | G06V 10/145 |
| | | | | 382/209 |
| 7,141,786 | B2 * | 11/2006 | McGann | G01N 15/0618 |
| | | | | 250/288 |
| 7,180,441 | B2 * | 2/2007 | Rowe | G01S 7/411 |
| | | | | 342/179 |
| 7,365,536 | B2 * | 4/2008 | Crowley | G01R 33/441 |
| | | | | 324/307 |
| 7,594,422 | B2 * | 9/2009 | Perry | G01N 1/2214 |
| | | | | 73/1.02 |
| 7,666,356 | B2 * | 2/2010 | O'Donnell | G01N 33/0057 |
| | | | | 73/863.56 |
| 7,721,588 | B2 * | 5/2010 | Perry | G01N 1/2205 |
| | | | | 73/864.33 |
| 7,750,631 | B2 * | 7/2010 | Crowley | G01R 33/441 |
| | | | | 324/309 |
| 7,942,033 | B2 * | 5/2011 | Jenkins | G01N 1/2205 |
| | | | | 73/864.33 |
| 8,129,691 | B2 * | 3/2012 | Hu | G01N 1/02 |
| | | | | 250/390.01 |
| 8,272,280 | B2 * | 9/2012 | Jones, Jr. | A22B 5/007 |
| | | | | 73/31.02 |
| 8,429,987 | B1 * | 4/2013 | Linker | G01N 1/22 |
| | | | | 73/864.33 |
| 8,614,582 | B2 * | 12/2013 | Syage | G01N 33/0057 |
| | | | | 324/464 |
| 8,701,463 | B2 * | 4/2014 | Brasfield | G01N 33/0001 |
| | | | | 73/23.34 |
| 9,103,763 | B2 * | 8/2015 | Dayan | G01N 33/0057 |
| 9,134,205 | B2 * | 9/2015 | Hillis | G01N 1/22 |
| 9,303,446 | B2 * | 4/2016 | Fougeroux | E06B 5/00 |
| 11,053,729 | B2 * | 7/2021 | Romero | E06B 3/90 |
| 11,149,453 | B2 * | 10/2021 | Slagel | E04H 1/00 |
| 11,401,747 | B2 * | 8/2022 | Romero | E05F 15/608 |
| 11,415,490 | B2 * | 8/2022 | Fry | G01N 1/2202 |
| 2001/0049926 | A1 * | 12/2001 | Davies | G01N 1/2214 |
| | | | | 55/385.2 |
| 2003/0041573 | A1 * | 3/2003 | Davies | B08B 5/02 |
| | | | | 55/385.2 |
| 2003/0085348 | A1 * | 5/2003 | Megerle | G01N 1/2202 |
| | | | | 250/361 R |
| 2004/0166550 | A1 * | 8/2004 | Sullivan | G01N 33/53 |
| | | | | 435/7.94 |
| 2005/0057354 | A1 * | 3/2005 | Jenkins | G07C 9/38 |
| | | | | 340/552 |
| 2006/0081073 | A1 * | 4/2006 | Vandrish | G01N 1/2202 |
| | | | | 73/864.33 |
| 2006/0243902 | A1 * | 11/2006 | Altes Royo | G01N 27/622 |
| | | | | 250/288 |
| 2009/0044641 | A1 * | 2/2009 | Konduri | G01N 1/2273 |
| | | | | 73/864.33 |
| 2010/0245081 | A1 * | 9/2010 | Arcaini | G01N 30/00 |
| | | | | 340/540 |
| 2011/0272574 | A1 * | 11/2011 | Mitko | G01N 27/622 |
| | | | | 250/287 |
| 2013/0334419 | A1 * | 12/2013 | Kluczynski | G01J 3/42 |
| | | | | 250/339.13 |

OTHER PUBLICATIONS

Bohannon, R.W., et al., "Comfortable and Maximum Walking Speed of Adults Aged 20-79 Years: Reference Values and Determinants," Age and Ageing, Jan. 1997, vol. 26, No. 1, pp. 15-19.

Fabian, P., et al., "Influenza Virus in Human Exhaled Breath: An Observational Study," PloS ONE, Jul. 2008, vol. 3, Issue 7, p. e2691, 6 pages.

Hök, B., et al., "Contactless Measure of Breath Alcohol," Micro Structure Workshop, Vasteras, Sweden, May 10, 2006, 3 pages.

International Search Report in corresponding/related International Application No. PCT/IB2019/057613, dated Feb. 10, 2020.

Korelin, I.A., et al., "Rationale Choosing Interval of a Piecewise-Constant Approximation of Input Rate of Non-Stationary Queue System," Journal of Physics: Conference Series, Jan. 1, 2018, vol. 944, 012060, 8 pages, IOP Publishing.

Ladhani, L., et al., "Sampling and Detection of Airborne Influenza Virus Towards Point-of-Care Applications," PLoS ONE, Mar. 28, 2017, vol. 12, Issue 3, 15 pages.

Miekisch, W., et al., "Diagnostic Potential of Breath Analysis—Focus on Volatile Organic Compounds." Clinica Chimica Acta; Apr. 16, 2004, vol. 347, pp. 25-39, Elsevier B.V.

Park, K.-T., et al., "Detection of Airborne Viruses Using Electro-Aerodynamic Deposition and a Field-Effect Transistor," Scientific Reports, Dec. 8, 2015, vol. 5, 10 pages.

Saylan, Y., et al., "An Alternative Medical Diagnosis Method: Biosensors for Virus Detection," Biosensors, May 21, 2019, vol. 9, No. 65, 22 pages.

Shen, F., et al., "Integrating Silicon Nanowire Field Effect Transistor, Microfluids and Air Sampling Techniques for Real-Time Monitoring Biological Aerosols," Environmental Science & Technology, Sep. 1, 2011, vol. 45, No. 17, pp. 7473-7480.

Tang, J.W., et al., "Airflow Dynamics of Human Jets: Sneezing and Breathing—Potential Sources of Infectious Aerosols," PLoS ONE, Apr. 1, 2013, vol. 8, Issue 4, 7 pages.

Written Opinion of the International Searching Authority in corresponding/related International Application No. PCT/IB2019/057613, dated Feb. 10, 2020.

Xu, Z., et al., "Molecular and Microscopic Analysis of Bacteria and Viruses in Exhaled Breath Collected Using a Simple Impaction and Condensing Method," PLoS ONE, Jul. 2012, vol. 7, Issue 7, p. e41137, 8 pages.

Nanometer Aerosol Sampler, Model 3089, TSI Incorporated, downloaded Dec. 19, 2018 (www.flir.com/products/ibac-2/).

(56) References Cited

OTHER PUBLICATIONS

Polaron F10, Real-Time Bioaerosol Sensor, Air Techniques International, downloaded Nov. 7, 2019 (www.atitest.com/products/polaron-f10-real-time-bioaerosol-sensor/).

* cited by examiner

| No. of Puffs | 1 | 2 | 2 | 2 | 2 | 2 | 3 | 4 |
|---|---|---|---|---|---|---|---|---|
| Min. air speed | 3.69 | 11.04 | 14.71 | 18.38 | 22.05 | 25.73 | 18.38 | 25.73 |
| Sampling time | 0.3571 | 0.1190 | 0.0893 | 0.0714 | 0.0595 | 0.0510 | 0.0714 | 0.0510 |
| Pause time | 0 | 0.1190 | 0.1785 | 0.2143 | 0.2381 | 0.2551 | 0.0714 | 0.0510 |

FIG. 8

| Parameter | Description | Design Range |
|---|---|---|
| $w_c$ | corridor width | $1.11\text{m} - 1.5\text{m}$ |
| $D$ | air puffer separation distance | $2w_c - 4w_c$ |
| $\ell_p$ | air puffer slot length | $1\text{m} - 1.1\text{m}$ |
| $w_p$ | air puffer slot width | $0.1\text{m} - 0.5\text{m}$ |
| $\ell_d$ | detector array length | $\ell_p - 1.2\ell_p$ |
| $w_d$ | detector array width | $w_p - 1.2w_p$ |
| $t_s$ | sampling time | less than $0.3571$ s |
| $u_z$ | airflow speed | $u_z = \frac{w_c + \widetilde{\ell}_z}{2t_s} + \frac{0.0107}{\sqrt{t_s}}$ |

FIG. 9

```
┌──────────────────────────────────────────────────────────────┐
│  DIRECTING AN INDIVIDUAL, THROUGH AN ACCESS GATE, TO A       │──1000
│  CORRIDOR EXTENDING ALONG A LONGITUDINAL AXIS                │
└──────────────────────────────────────────────────────────────┘
                               │
                               ▼
┌──────────────────────────────────────────────────────────────┐
│  DETECTING A PRESENCE OF THE INDIVIDUAL WITH A PERSON        │──1002
│  DETECTION SYSTEM LOCATED IN THE CORRIDOR                    │
└──────────────────────────────────────────────────────────────┘
                               │
                               ▼
┌──────────────────────────────────────────────────────────────┐
│  INITIATING A TESTING SET TO GENERATE AN AIR PUFF, WHICH     │
│  TAKES AN EXHALED BREATH OF THE INDIVIDUAL, TO A             │──1004
│  DETECTION SET, FOR DETERMINING A PRESENCE                   │
│  OF THE AIRBORNE MICROORGANISM                               │
└──────────────────────────────────────────────────────────────┘
                               │
                               ▼
┌──────────────────────────────────────────────────────────────┐
│  ANALYZING WITH THE DETECTION SET THE AIRBORNE               │──1006
│  MICROORGANISM                                               │
└──────────────────────────────────────────────────────────────┘
```

FIG. 10

AIRBORNE ORGANIC MATTER DETECTION SYSTEM AND METHOD

CROSS-REFERENCE TO RELATED APPLICATIONS

This application is a U.S. National Stage Application of International Application No. PCT/IB2019/057613, filed on Sep. 10, 2019, which claims priority to U.S. Provisional Patent Application No. 62/736,586, filed on Sep. 26, 2018, entitled "VIRAL AEROSOL DETECTION SYSTEM," the disclosure of which is incorporated herein by reference in its entirety.

BACKGROUND

Technical Field

Embodiments of the subject matter disclosed herein generally relate to a system for detecting airborne organic matter present in human exhaled air, and more particularly, to a system that can handle a flow of a large amount of people present during mass gatherings and is configured to test each individual from the mass gathering for organic matter while the individual is in motion.

Discussion of the Background

Human breathing is a process that involves the interaction of internal organs (lungs) with the ambient air, i.e., the atmosphere. Thus, it is very likely that the exhaled breath from any individual contains "footprints" associated with the internal body of the individual. Such a footprint may contain either life forms (e.g., bacteria, spores, viruses, which are called herein microorganisms) that do not naturally reside on or within the individual, or may also contain volatile organic compounds (VOCs) that naturally inhabit the human body. Thus, the term "organic matter" is understood in this application to include microorganisms, VOCs, or both. It is further noted that these terms are used herein interchangeable.

Various efforts have been made by the researchers to develop methods to analyze the exhaled breath in medicine and clinical research [1]-[4] as aerosol transmission of viruses serves as an essential mode of several viral infections such as influenza A virus, severe acute respiratory syndrome (SARS) virus, lyssavirus, rabies, and many other pandemics. Recently, the advances in several research fields encouraged the researchers to develop bio-sensors that can effectively collect aerosol samples and detect the existence of different viruses [5]-[7]. However, all the efforts mentioned above are made experimentally, in the lab, at a small scale, where microorganisms corresponding to a single individual are analyzed with various sensors, which is not appropriate for large mass gatherings. In other words, the current lab experiments for viral aerosol detection is limited to a single subject interacting with the existing sensors.

Mass gatherings take place when a large number of people (hundreds to tens of thousands or even more) converge to a single location for sports, recreational, social, religious, or any other kind of activities. During these mass gatherings, the vast movement of people from different regions poses a higher risk of diseases spread to far away places. In addition, the people act as a carrier for transporting emerging and/or reemerging diseases from their original locations to the gathering place. A high likelihood of disease transmission during mass gatherings is documents in the literature. A simple lab setup that can handle a single individual is not practical for such events.

To deal with this challenge, there is a need for a microorganism airborne detection system for mass gatherings that provides an effective and powerful solution to this problem.

BRIEF SUMMARY OF THE INVENTION

According to an embodiment, there is an aerosol detection system for detecting airborne organic matter. The detection system includes a corridor extending along a longitudinal axis and having first and second ends, an access gate connected to the first end of the corridor and configured to control access of an individual to the corridor, a person detection system located in the corridor and configured to determine the presence of the individual inside the corridor, and a testing set configured to generate an air puff, which directs an exhaled breath of the individual for determining a presence of the airborne organic matter. The corridor has a width $w_c$ that allows movement of a single individual past the testing set.

According to another embodiment, there is a method for detecting airborne organic matter. The method includes directing an individual, through an access gate, to a corridor extending along a longitudinal axis, detecting a presence of the individual with a person detection system located in the corridor, initiating a testing set to generate an air puff, which directs an exhaled breath of the individual, to a detection set, for determining a presence of the airborne organic matter, and analyzing with the detection set the airborne organic matter. The corridor has a width $w_c$ that allows movement of a single individual past the testing set.

According to still another embodiment, there is an aerosol detection system for detecting airborne organic matter, and the detection system includes a person detection system located in a corridor and configured to determine a presence of an individual passing through the corridor, and a testing set configured to generate an air puff, which directs an exhaled breath of the individual to a sensor for determining a presence of the airborne organic matter. The testing set generates the air puff for a given sampling time $t_s$, and a speed $u_z$ of the air puff is selected based on the corridor width $w_c$, the sampling time $t_s$, and an actual exhaled breath $\tilde{\ell}_z$ of the individual, perpendicular on a longitudinal axis of the corridor.

BRIEF DESCRIPTION OF THE DRAWINGS

For a more complete understanding of the present invention, reference is now made to the following descriptions taken in conjunction with the accompanying drawings, in which:

FIG. 8 is a table that presents various parameters of the airborne organic matter detection system;

FIG. 9 is another table that indicates relationships between various parameters of the airborne organic matter detection system;

FIG. 10 is a flowchart of a method for determining the presence of airborne organic matter with the airborne organic matter detection system.

DETAILED DESCRIPTION OF THE INVENTION

Figure 1:
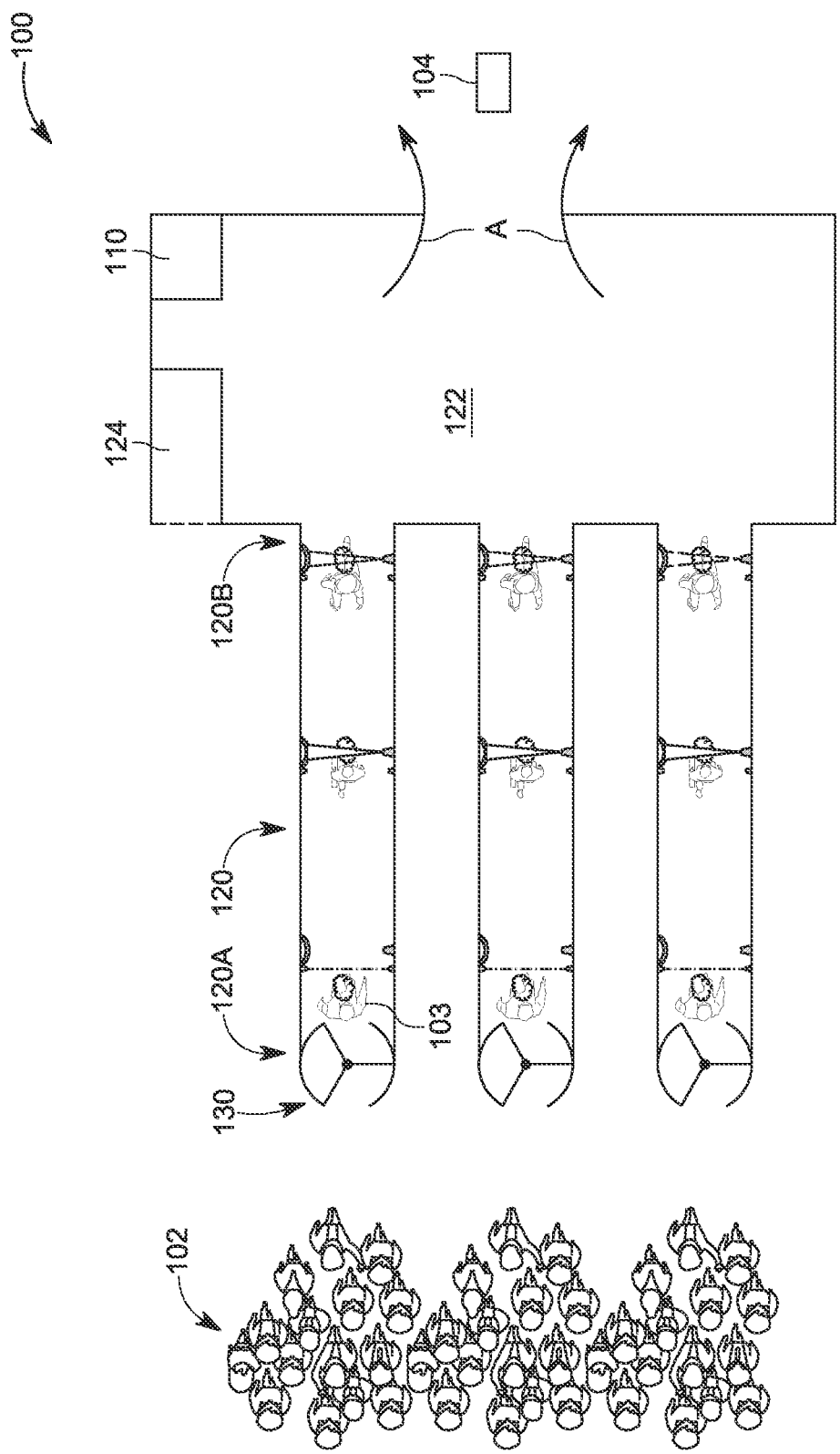
FIG. 1 is a schematic diagram of an airborne organic matter detection system that is appropriate for screening individuals that attend large mass gatherings.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a system that uses various air movement devices and air sensing devices for determining one or more airborne microorganisms that are damaging to a human being. However, the embodiments to be discussed next are not limited to detecting one or more organisms associated with the human being, but they may be applied to determining a footprint for non-human beings, i.e., cattle or other farm raised animals.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an airborne organic matter system is implemented as special smart corridors in order to accommodate massive pedestrian flows and detect suspicious cases that will be examined in the medical quarantine. The corridors are equipped with control gates, infra-red sensors, air puffers, and airborne organic matter detectors. The control gates are used to limit the number of humans flowing into the corridors, to guarantee robust detection performance and suit the massive number of people to be examined. Multiple air puffers and airborne organic matter bio-sensors are used to minimize both viral miss-detection and false alarm probabilities. In one application, video cameras may be installed in the corridor and/or at the control gates for providing images of the humans entering the corridors, to a control center. The control center may be equipped with face recognition software for identifying the person that is suspected of carrying an infectious organism so that the person can be placed in quarantine until medical treatment can be administered. Further, the system may have a special corridor to accommodate those people that require special attention, e.g., people that are not mobile and need to use any device (e.g., a mobile chair) for moving through the corridor. For this corridor, the placement of the testing set is adjusted to capture the breath of a person that sits in such a chair.

To implement the existing sensors used in the lab for detecting organic matter, it is needed a large mass viral aerosol detecting system that can handle the movement of a large amount of people and at the same time, can individually sample each of the moving people. This kind of system is designed and sized based on the various characteristics of the people to be processed, as for example, height of the people, walking speed, sensor capability, etc. To account for some of these variables, it is necessary to model the breathing process of the people to be processed. For this reason, the design of the novel system is discussed first, followed by a model of the breathing process and how this model affects the specific dimensions of the novel system.

FIG. 1 illustrates an airborne organic matter detection system (AOMDS) 100 that is implemented in a controlled indoor environment that is monitored by a control center 110, which is discussed later. To accommodate a large crowd 102 of individuals without impeding their flow to a given event that takes place at a location 104, according to this embodiment, the AOMDS 100 employs several smart examination corridors 120 (only one is labeled for simplicity; although the figure shows only three such corridors, one skilled in the art will understand that fewer or more corridors may be used). Each smart examination corridor 120 has at a first end 120A, that is facing the crowd 102, and this end is controlled by an electrical and/or mechanical gate 130. This means that access of each individual from the crowd 102 to the event location 104 is directed through one of the corridors 120 and no other access path is provided to the event. Thus, each individual 103 from the crowd 102 enters at the first end 120A, through the gate 130, into the corridor 120, interacts within the corridor, in a non-invasive way, with one or more air puffs generated in the corridor, and then exits the corridor 120 at a second end 120B, into a lobby area 122. Those individuals that are identified by the control center 110 as potential carriers of targeted organic matter (for example, an infectious microorganism, or a VOC that is associate with a disease) are diverted to a control and medical quarantine area 124, while the rest of the individuals can proceed to the event/gathering place 104 as indicated by arrows A. In one embodiment, there is no need for any person to stop while the exhaled airborne organic matter is processed. In one application, there is no need for the individual to even slow down while passing the corridor 120.

At least one smart examination corridor 120, which is shown in more detail in FIG. 2, includes side walls 202 and 204 connected to each other by a ceiling wall 206. A width of the corridor 120, i.e., a distance between the walls 202 and 204, is illustrated as $w_c$ in the figure. The side walls extend along a longitudinal direction x of the corridor. For illustration purposes, FIG. 2 shows only partially the ceiling wall 206. The side walls 202 and 204 and the ceiling wall 206 can be made of any material. The side walls 202 and 204 may be fixedly or removably attached to a floor. The floor may be the ground, the floor of a building where the mass gathering is taking place, or a panel of a desired material that is tightly attached to the side walls for forming an almost sealed cavity 210 inside the corridor 120. The joints between the side walls and the floor and the ceiling may be made to be fully sealed (i.e., they may be sealed with a sealant to prevent any air to ingress or egress the cavity). In one embodiment, the joints are tight but not sealed, so that air still can be exchanged between the cavity of the corridor and the ambient.

FIG. 2 also show the gate 130 attached to the first end 120A of the corridor 120. The gate 130 may be a revolving gate that includes a rotating frame 230 that has plural openings 232 that rotate along a central pole 234. A motor 236 may be connected to the central pole 234 to control the rotation of the revolving gate. The control center 110 may be in communication with the motor 236 so that the operator of the control center can regulate the number of individuals that enter the corridor 120 for a given time period. The control center 110 may also close access to the corridor 120 by stopping the revolving gate, so that when an individual 103 inside the corridor is suspected of being a carrier of an infectious microorganism, that individual can be isolated from the crowd.

Figure 2:
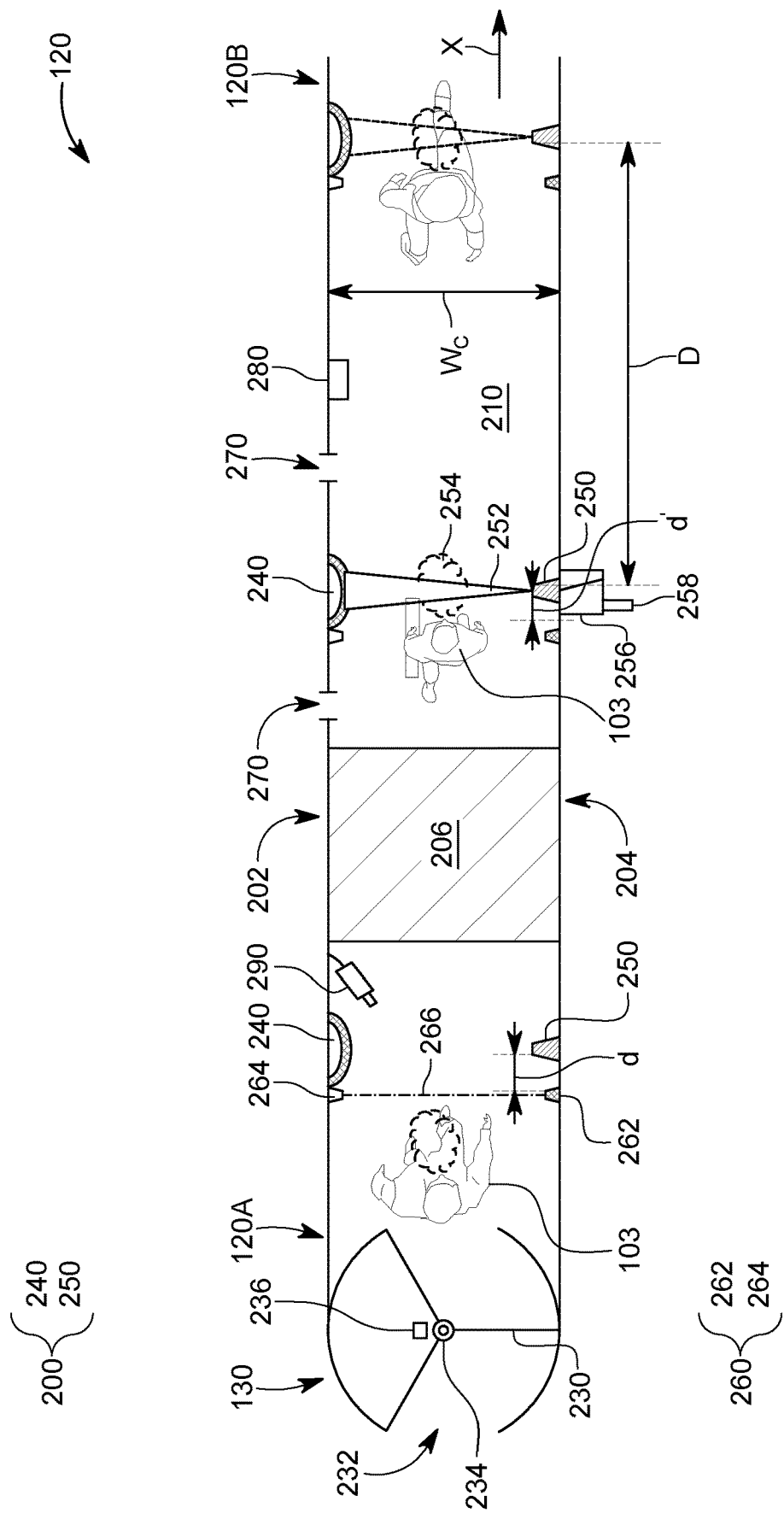
FIG. 2 illustrates a corridor that is part of the airborne organic matter detection system.

The corridor 120 may also include one or more testing sets 200. A testing set 200 includes a detection set 240 mounted on one wall, for example, wall 202 in the figure, and one or more air puffers 250 mounted on an opposite wall of the corridor, for example, wall 204. FIG. 2 shows three detection sets 240 and three air puffers 250 separated by a distance D along the longitudinal axis X. However, one skilled in the art will understand that fewer or more detections sets and/or air puffers may be used.

A detection set 240 includes one or more sensors that are configured to measure the presence of various chemical signatures associated with known infectious microorganisms and/or selected VOCs. For example, a field effect transistor (FET) may be used as such a sensor and changes in the conductance of the channel of the FET due to selective binding of specific proteins or nucleic acid sequences may trigger the presence of the airborne microorganism. In addition, the considerable progress that has been made in microfluidic channels has enabled the efficient transport of virus-laden fluids onto specific-antibody-coated FET transistors. Those skilled in the art will understand that any known sensor may be used as long as that sensor is capable of detecting the presence of specific proteins or nucleic acid sequences, or any other substance specific for airborne microorganisms or selected VOCs.

An air puffer 250 is used to direct the airborne organic matter exhaled by a given individual toward the detection set 240. An air puffer is a device that generates a high-speed airflow that is configured to take the aerosol particulates exhaled by the individual 103, when inside the corridor 120, and move them toward a desired location. In this embodiment, the desired location is the location of the detection set 240. In this way, part of the exhaled air from the passing individual 103 is taken by the high-speed airflow and directed toward the detection set 240 for analysis.

FIG. 2 shows that the air puffer 250 generates the high-speed air flow (or air puff) 252 right when the exhaled air 254 is exhaled by individual 103. This coordination between the air puff and the exhaled air is achieved, in one application, by placing a person detection system 260 upstream the detection set 240 and the air puffer 250 (by a distance d) so that only when the person detection system 260 detects the presence of the individual 103, the air puffer 250 is activated. In one application, the person detection system 260 includes an infra-red signal transmitter 262 and an infra-red sensor 264. The infra-red signal transmitter 262 generates an infra-red beam 266, which is detected by the infra-red sensor 264. However, when the individual 103 is approaching the air puffer 250, that person breaks the infra-red beam 266 and the infra-red sensor 264 fails to detect it. Because the infra-red signal transmitter 262 and the infra-red sensor 264 are connected to the control center 110, the control center determines when the infra-red beam 266 is interrupted and activates the air puffer 250. In this way, the generation of the high-speed air jet 252 is synchronized with the exhaled air 254 exhaled by the person 103 to intersect with each other.

Figure 3:
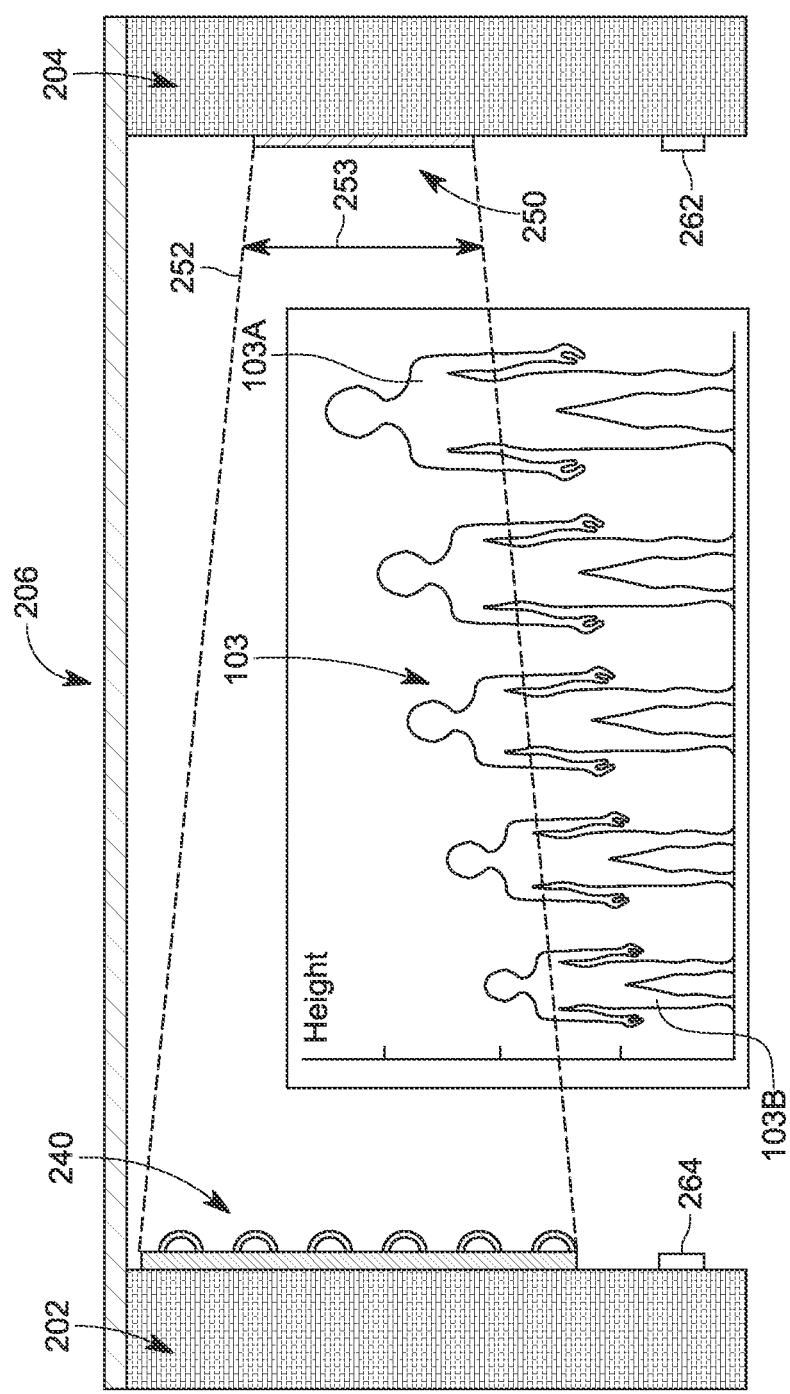
FIG. 3 illustrates a cross-section through the corridor of the airborne organic matter detection system.

A cross-sectional view of the corridor 120 is shown in FIG. 3. Note that the size of the air puffer 250 is so selected that a cross-section 253 of the high-speed air flow 252 is large enough to interact with the exhaled air from any individual 103, i.e., a fully grown adult 103A or a child 103B. The detection set 240 is sized correspondingly, as also shown in FIG. 3, so that the exhaled air from different height individuals is received for analysis.

By spacing the detection sets 240 and the air puffers 250 along the longitudinal axis x of the corridor 120 as shown in FIG. 2, a spatio-temporal separation between the plural testing sets 200 is obtained. The testing sets are installed apart with a predefined minimum distance and the entry control gate 230 is used to limit the people flow through the corridor. As such, both viral miss-detection and false alarm decreases, yielding a robust viral detection system.

In one application, the walls and/or floor of the corridor are manufactured to absorb microorganisms or VOCs and prevent them from spreading. For example, as illustrated in FIG. 2, it is possible to have selected locations where one or more vents 270 are formed to allow the contaminated air to exit the corridor. In this regard, note that each air puffer 250 may be connected to a pump 256, located, for example, outside the corridor, which has an inlet 258 for taking in clear air from outside the corridor (or the building where the corridor is located) and accelerating it to form the high-speed air flow 252. Part of this air jet, after mixing with the exhaled air 254 from the individual 103, is then discharged outside the corridor 120 through the vents 270. The vent 270 may be a passive vent (i.e., it has no moving element for moving the air out of the corridor) or an active vent (i.e., it includes a fan or similar device for forcing the air from inside the corridor out). In another application, the walls of the corridor may be coated with a chemical substance that kills germs. In still another application, cyclic sanitations may be periodically performed to remove the germs. For example, it is possible that ultraviolet (UV) lights 280 are installed inside the corridor and used to kill the germs. The control center 110 can be configured to automatically lock the gates 230 before the UV lights 280 are turned on so that no individual is present inside the corridor when the sanitation action takes place. In one embodiment, two or more of these methods may be employed at the same time, e.g., force the air to move outside the corridor through the various vents while also having the UV lights on. Those skilled in the art will understand that other ways for sanitizing the air inside the corridor may be used or added to the above discussed methods.

As discussed above, the length and location of the air puffers are designed based on the corridor's width, and the minimum and maximum heights of the passing people. As a result, the locations of the bio-sensors can be determined by studying the air puff signature on the other side of the corridor. In the following embodiments, it is assumed that two modes of an air puffer operation are used, the sampling mode and the sanitizing mode. In the first mode, the air puffer 250 emits some puffs of air to collect the exhaled breath 254 of the passing individual 103, after which the air puffer stops, allowing some time for the exhaled breath 254 to diffuse to the detection set 240. The selection for the airflow speed, sampling time, and pause time for the systems is discussed next.

Figure 4:
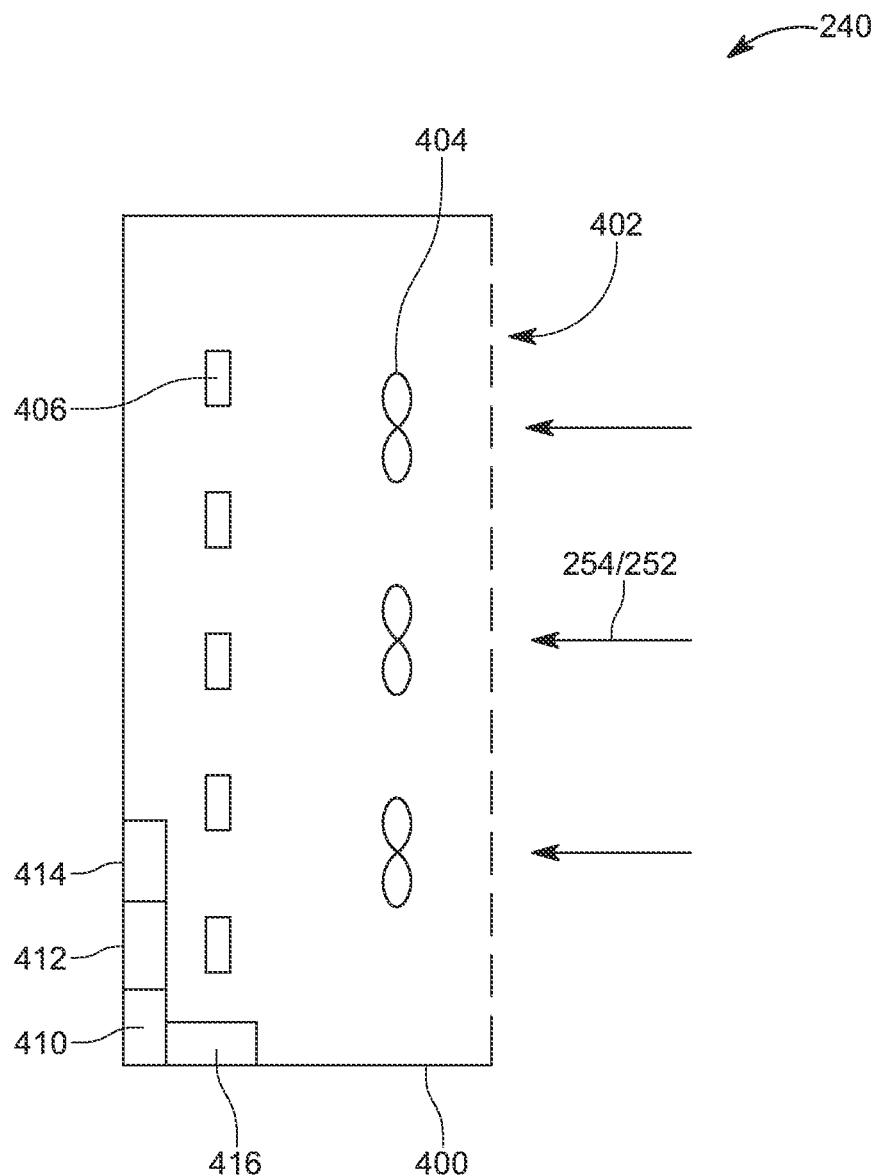
FIG. 4 illustrates a cross-section of a detection set that is part of the airborne organic matter detection system.

To increase the efficiency of the detection process, the detection set 240, as illustrated in FIG. 4, may include in addition to ports 402, formed in a housing 400, one or more air samplers 404 (for example, fans) that force the air puffs 254 inside the housing 400 and absorbs them completely, without reflection, and then apply the air puffs 254 to one or more sensors 406, which are configured to detect infectious microorganisms and/or VOCs. Any known sensor may be used as sensor 406, for example, electrochemical, optical and piezoelectrical based sensors [11]. Optical based aerosol sensors are one of the fastest bio-sensors such as the ones based on UV laser induced florescence (LIF), photoionization, and polarized elastic light scattering, which has the ability to reduce the analysis time to 1 second. Examples of commercial products include FIR IBAC 2 [12] and Polaron F10 [13]. The number of sensors depends on the microorganisms and/or VOCs that need to be considered in the detection process.

The housing 400 may also have a local processor 410 that coordinates the air samplers 404 and sensors 406. For example, the local processor 410 instructs a power source 412 to provide electrical power to the air samplers and the sensors. Data from the sensors 406 is communicated to the processor 410, which can partially or fully analyze it. A memory 414 is also connected to the processor for storing such data. The data may be transmitted to a global processor of the control center 110, through a transceiver 416, for further analysis and decision making. The transceiver 416 may be implemented as a wired or wireless device as known in the art. Some of the sensors 406 have a limited lifetime, so several backup sensors can be also provided inside the housing 400 to allow a long testing time.

Figure 5:
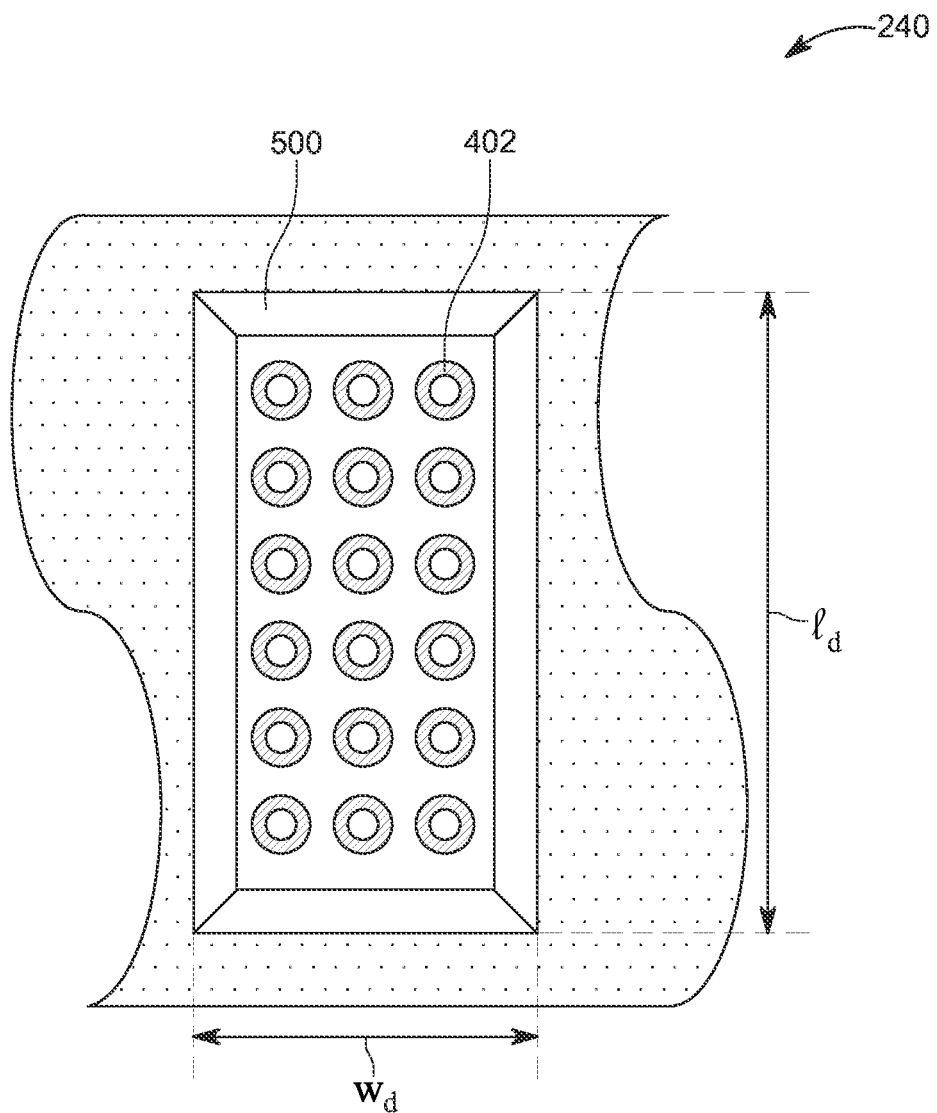
FIG. 5 illustrates a front view of the detection set that is part of the airborne organic matter detection system.
Figure 6:
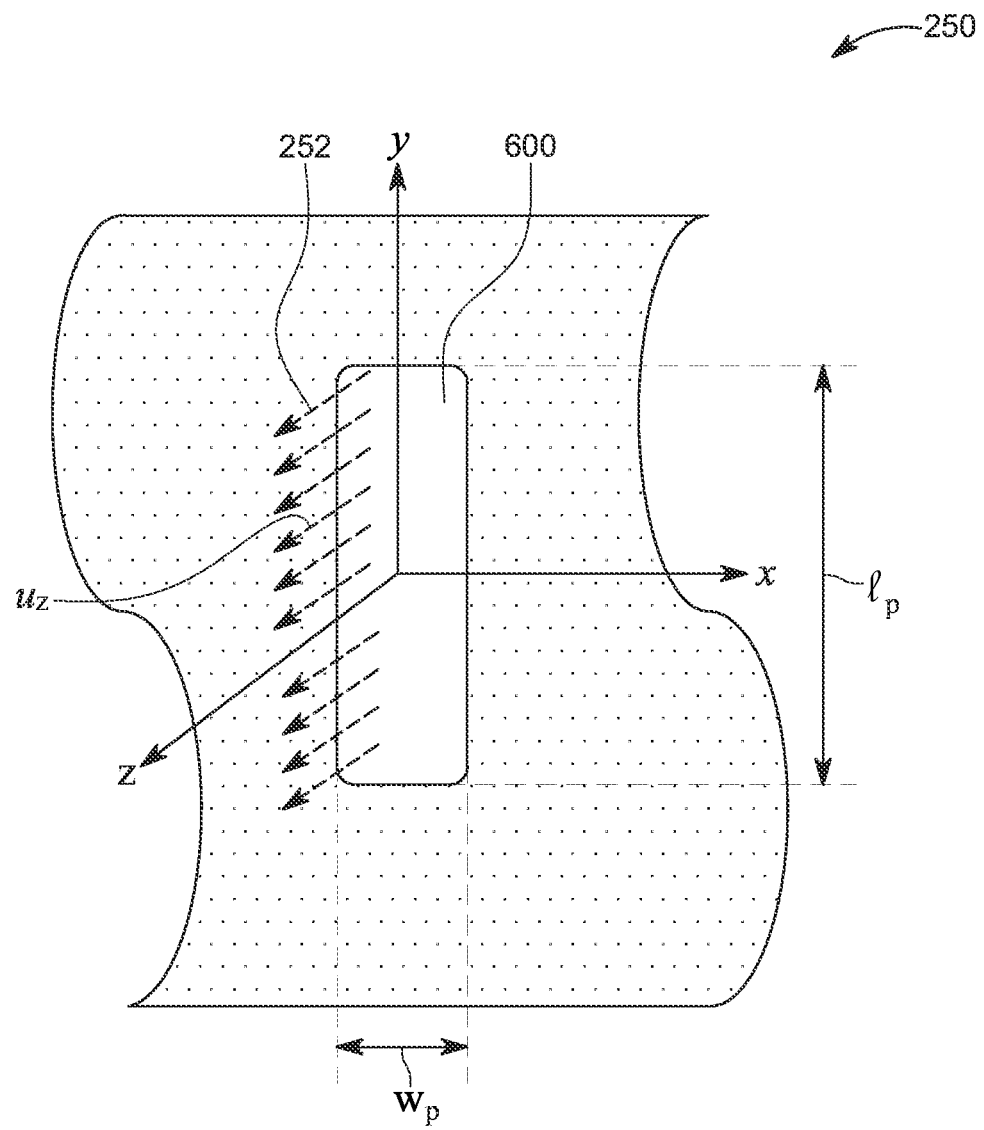
FIG. 6 illustrates a front view of an air puffer that is part of the airborne organic matter detection system.

While the previous figures were used to describe the AOMDS system 100 without a specific focus on the sizes of the various parts, the next figures are used to illustrate how one or more sizes of the various parts of the corridor are selected for efficiently being able to detect the infectious microorganisms or VOCs. In this regard FIG. 5 shows a front face 500 of the detection set 240 and FIG. 6 shows a front face 600 of the air puffer 250. Each of the figures illustrate a length and width of these front faces. Note that the detection set 240 has plural vents 402 provided on the front face 500 while the front face 600 of the air puffer 250 is a single long slot. In one application, the front face 600 of the air puffer 250 may have plural slots, which may be long as shown in FIG. 6, or have a different shape, for example, a square.

The corridor width $w_c$, which is shown in FIG. 2, needs to have a minimum size in order to increase the probability of detection. Based on the international building codes that regulate such sized for mass gathering events, the corridor width can have the following range 1.11 to 1.5 m, to allow a smooth movement of the individuals and increase the probability of infectious microorganism or VOCs detection. Regarding the distance D between different air puffers 250 along the longitudinal axis x, also illustrated in FIG. 2, it is selected to prevent the interference between different people's microorganism signature. Thus, in one embodiment, the distance D is selected to be between $2w_c$ and $4w_c$ m.

The air puffer 250's slot 600 illustrated in FIG. 6 is selected to have a length $\ell_p$ and a width wp to account for different human heights and capture the spatial exhaled breath 254 illustrated in FIG. 2. To this end, the air puffer 250 is installed approximately 0.8-1 m above the ground level, with $\ell_p$=1 m or larger to serve people with heights from 1 to 2 m. The exhaled breath profile 254 propagates for 0.6 m, toward the detection set 240, with a speed of about 1.4 m/s, according to some recent experiments [8], which is approximately equal to the average walking speed for humans [9].

The air puffer 250 is controlled by the control center 110 to start emitting the sampling puffs 252 once the individual 103 is 0.5 m away from it (i.e., the distance d between the person detection system 260 and the air puffer 250 is about 0.5 m). The same control center 110 is programmed to instruct the air puffer 250 to stop generating air puffs when the individual 103 is a distance d' of 0.1 to 0.2 m upstream from the air puffer 250, along the longitudinal axis x, to avoid the direct exposure of the individual to the high-speed airflow 252. The distance d' is calculated based on the walking speed of the individual, the width $w_c$ of the corridor, and the speed of the air flow or puff 252 generated by the air puffer 250. For these values, the width $w_p$ of the slot 600 is chosen to be 0.1-0.5 m to maximize the probability of capturing the breath air 254.

Figure 7:
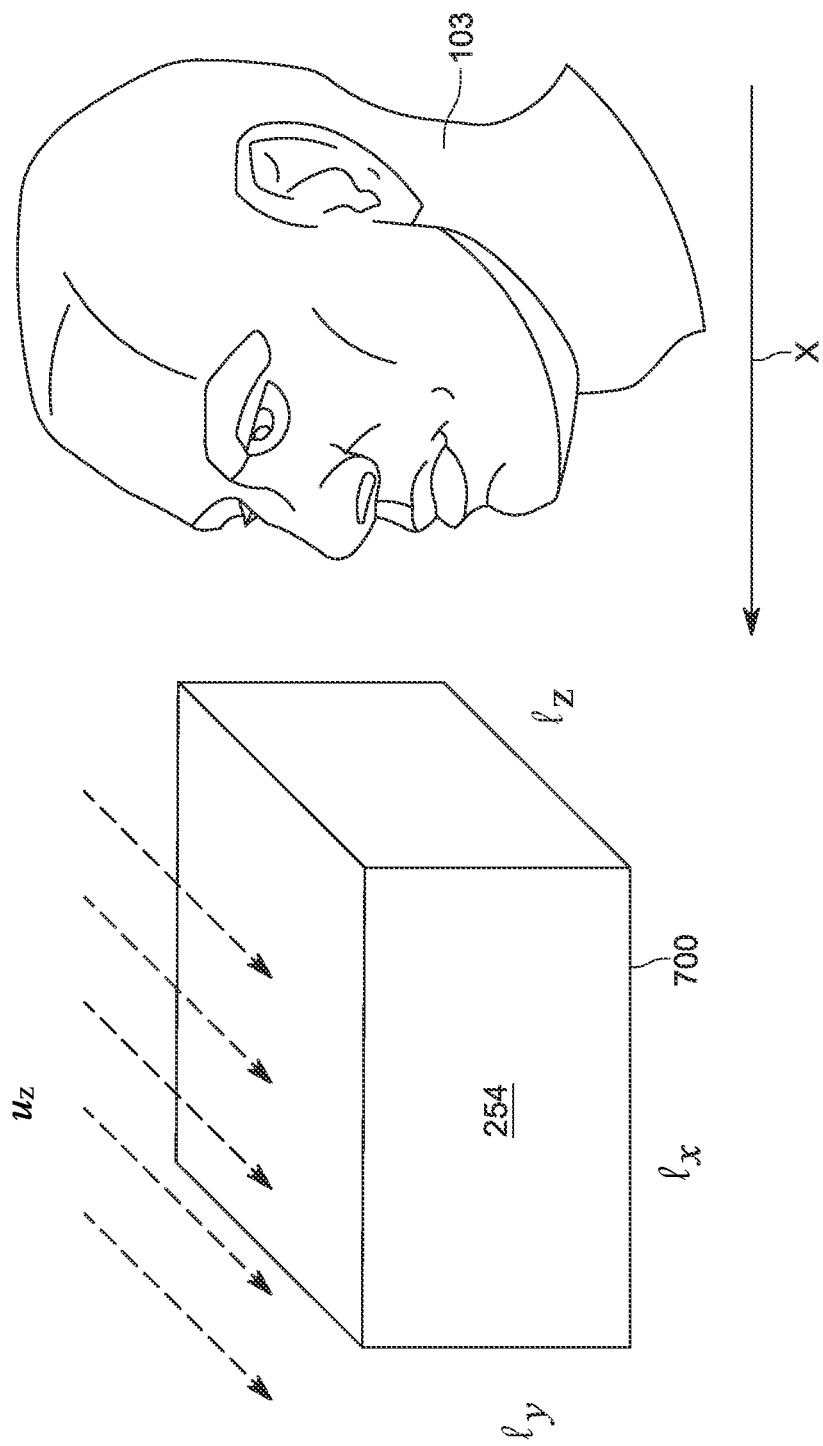
FIG. 7 is a schematic representation of exhaled breath from an individual.

The air puff's velocity $u_z$, exposure, and sampling time are selected based on a model to be discussed next, to improve the detection of the infectious microorganism or VOC. The viral concentration of the air puff arriving at the detection set 240 needs to be calculated according to the model. Although the shape of the exhaled air 254 is not uniform, in this model, the shape of the exhaled air is approximated by a regular size box to simplify the analysis. To this end, it is assumed that the exhaled air's shape is cuboid, located just in front of the individual 103, as illustrated in FIG. 7 by box 700. The box 700, which is assumed to include the exhaled air 254, has three sides defined by lengths $\ell_x$, $\ell_y$, and $\ell_z$, which can take the following values: $\ell_z$=0.6-0.8 m, $\ell_x$=0.18-0.23 m and $\ell_y$=0.18-0.23 m, based on the results in [8].

The exhaled human breath acts as a continuous source in the x direction, which coincides with the walking direction of the individual 103. On the other hand, the slotted air puffer 250 takes samples and directs them to the other side of the corridor 120, which makes the collected samples act as instantaneous sources. To derive the spatial-temporal concentration of the airborne microorganism and/or VOC due to the instantaneous cuboid finite area 700, the model assumes a uniform distribution of the organic matter. Note that the model assumes that the organic matter includes aerosols, i.e., they are airborne when propagating from the individual 103 to the detection set 240.

With these assumptions, let an instantaneous viral point source, located at cuboid center $(x_o, y_o, z_o)$, emit Q viral aerosols and be subject to an airflow along the z direction with the velocity $u_z$ (see FIG. 6). The spatial-temporal concentration C due to this point source is expressed as in [10], by:

$$C_{point}(x, y, z, t) = \frac{Q}{(2\pi)^{3/2}\sigma^3}\exp\left[-\frac{(x-x_0)^2 + (y-y_0)^2 + (z-z_0-u_zt)^2}{2\sigma^2}\right], \quad (1)$$

where $\sigma=[2Dt]^{1/2}$ and D is the diffusivity, with a typical value of $1.5\times10^{-5}$ m$^2$ s$^{-1}$ for the molecular diffusivity of air [10]. To find the emitted temporal spatial viral aerosols due to the cuboid 700, a point source of Qdx'dy'dz' is considered and this source is integrated with respect to different locations x', y', and z' in the cuboid region 700 as follows:

$$C_{cuboid}(x, y, z, t) = \int_{x_0-\ell_x/2}^{x_0+\ell/2}\int_{y_0-\ell_y/2}^{y_0+\ell_y/2}\int_{z_0-\ell_z/2}^{z_0+\ell_z/2} \frac{Q}{(2\pi)^{3/2}\sigma^3} \times \quad (2)$$

-continued $$\exp\left[-\frac{(x-x')^2+(y-y')^2+(z-z'-u_z t)^2}{2\sigma^2}\right]dx'\,dy'\,dz'.$$

After evaluation equation (2), the viral aerosol concentration $C_{cuboid}$ is obtained as follows:

$$C_{cuboid}(x, y, z, t) = \frac{Q}{6}\text{erf}\left(\frac{\frac{\ell_x}{2}+(x-x_0)}{\sqrt{2}\sigma}\right)+ \tag{4}$$

$$\text{erf}\left(\frac{\frac{\ell_x}{2}+(x-x_0)}{\sqrt{2}\sigma}\right)\times\left[\text{erf}\left(\frac{\frac{\ell_x}{2}+(y-y_0)}{\sqrt{2}\sigma}\right)+\text{erf}\left(\frac{\frac{\ell_x}{2}+(y-y_0)}{\sqrt{2}\sigma}\right)\right]\times$$

$$\left[\text{erf}\left(\frac{\frac{\ell_z}{2}+(z-z_0-u_z t)}{\sqrt{2}\sigma}\right)+\text{erf}\left(\frac{\frac{\ell_z}{2}-(z-z_0-u_z t)}{\sqrt{2}\sigma}\right)\right].$$

The total viral amount located in the cuboid 700 needs to be collected after a sampling time $t_s$, after applying the air puffer. Thus, the viral collected amount at the detection set 240 is computed by integrating equation (3) over the detection set 240's area (given by the product of $\ell_d$ and $w_d$ in FIG. 5) after $t_s$ seconds, which is given by:

$$C_{detector}=\int_{sampling\ area, t=0\ to\ t_s} C_{cuboid}(x,y,z,t)|_{z=w_c}. \tag{4}$$

Thus, the values of the airflow velocity $u_z$ and sampling time $t_s$ are chosen to allow most of the viral aerosol calculated with equation (4) to be transferred to the housing 400 of the detection set 240 (see FIG. 4), which completely absorbs the received aerosols as previously discussed. As such, the product $u_z t_s$ is chosen to allow the Gaussian distribution of the organic matter to enter the housing 400 in the z direction. In one embodiment, the product $u_z t_s$ is selected to achieve the following condition, assuming the individual 103 walks along the corridor 103 along a center line, $$u_z t_s = \frac{w_c+\tilde{\ell}_z}{2}+1.96\sqrt{2Dt_s}, \tag{5}$$

where the second term is used to guarantee that at least 95% of the organic matter in the cuboid volume is captured by the housing 400, and $\tilde{\ell}_z$ represents the actual exhaled breath in the sampling area, which is located at the detector side, i.e., with $z=w_c$, and the maximum sampling area equals the detector area, i.e., $\ell_d w_d$, and the air collection (sampling) continues for $t_s$ seconds, which corresponds to a scenario in which a person is approaching the sampling area, and thus, it is not fully loaded. For $w_c=1.11$ m and $\tilde{\ell}_z=0.20$ m, and the typical value of D discussed above, the air flow 252 velocity is computed based on:

$$u_z = \frac{1.31}{t_s}+\frac{0.0107}{\sqrt{t_s}}. \tag{6}$$

As can be seen from equation (6), there are an infinite number of choices for the values of $u_z$ and $t_s$. In this embodiment, the values are chosen to allow taking several samples by emitting more short puffs. As it was previously mentioned, the air puffer operates once the individual 103 is d (e.g., 0.5 m) away and upstream of the air puffer 250. The air puffer needs to stop when the individual is about 0.1 m from the air puffer. Thus, the total available time considering a 1.4 m/s walking speed becomes, for the numbers selected herein, 0.3571 s. The table shown in FIG. 8 shows different possible options for the system 100, based on the model described by equations (4) to (6), for different numbers of air puffs.

The pause time $t_p$ allows some time for the exhaled breath air 254 to arrive at the puffing area (area at the intersection of the longitudinal axis x of the corridor and the direction of the jet 252 in FIG. 2), from where it is then moved to the detection set 240 by the air puffer 250. One can notice that the airflow speed increases with the increase of either the pause time or the number of air puffs. In one application, it is desirable to have a high-speed air puffer in order to prevent aerosol diffusion, which reduces its footprint on the detection set. This allows using less detector area, where the minimum area is the same as the air puffer's size. For the speed of air, the detection size's dimension should include aerosol diffusion outside of the air puffer area. In one embodiment, the detection dimension for the detection set can be chosen in the following range: $\ell_d=(1-1.2)\ell_p$ and $w_d=(1-1.2)w_p$. The table in FIG. 9 shows a summary of these design parameters for this embodiment. Although these values were found by the inventors to produce the most efficient AOMDS system 100, those skilled in the art will understand that a system that has variations from these dimensions may also work.

Returning to FIG. 2, it is possible to have one or more cameras 290 attached to the walls or the ceiling of the tunnel, just downstream of the testing set 200 so that when the individual 103 passes by, and the exhaled breath 254 is captured for analysis, a picture of the individual is taken so that the results of the exhaled breath 254 are matched to that specific individual. For example, it is possible that the camera 290 is connected to the control center 110. Thus, when the person detection system 260 is triggered by the presence of an individual 103, a signal indicative of this event is sent by the detection system 260 to the control center 110 and the control center 110 starts the camera 290 for recording the approaching individual. In one application, it is possible that the local controller 410 makes the decision to start the camera. After the detection set 240 records the data associated with the exhaled breath 254, that data together with the image of the individual 103 is sent to the control center 110 for further processing. If the control center 110 determines that suspicious organic matter might be present in the individual's exhaled breath, the image of that individual is provided at an operator of the corridor, at the second end 120B, to quarantine that individual for further tests.

A method for detecting airborne organic matter with the VDAS system 100 discussed above is now discussed with regard to FIG. 10. The method includes a step 1000 of directing the individual 103, through an access gate 230, to a corridor 120 extending along a longitudinal axis, a step 1002 of detecting a presence of the individual 103 with a person detection system 260 located in the corridor 120, a step 1004 of initiating a testing set 200 to generate an air puff 252, which takes an exhaled breath 254 of the individual 103, to a detection set 240, for determining a presence of the airborne organic matter, and a step 1006 of analyzing with the detection set 240 the airborne organic matter, where the corridor has a width $w_c$ that allows movement of a single individual past the testing set.

In one application, the corridor has opposite first and second walls, and the testing set includes an air puffer attached to the first wall and the detection set is attached to the second wall. The person detection system is located between the access gate and the testing set, and includes an infrared transmitter and an infrared sensor. The method may further include a step of controlling with a control center 110 the access gate to allow entry of a single individual into the corridor. In one application, the air puffer has a slot having a length $\ell_p$ and a width $w_p$, and the detection set has a length $\ell_d$ between $\ell_p$ and 1.2 $\ell_p$, and a width $w_d$ between $w_p$ and 1.2$w_p$. The method may further include a step of generating an airflow jet with the air puffer to have a speed $u_z$, which is oriented toward the detection set, and the detection set includes plural sensors, and/or a step of generating the airflow jet for a given sampling time $t_s$, and having a speed $u_z$, which is selected based on the corridor width $w_c$, the sampling time $t_s$, and an actual exhaled breath $\tilde{\ell}_z$ of the individual, perpendicular on the longitudinal axis of the corridor. In one application, the testing set includes plural air puffers distributed at a distance D from each other along the longitudinal axis, and the distance D is between two times and four times a width of the corridor, the testing set includes plural detection sets, disposed opposite to the air puffers, and configured to include plural sensors for determining the presence of the airborne organic matter.

Figure 11:
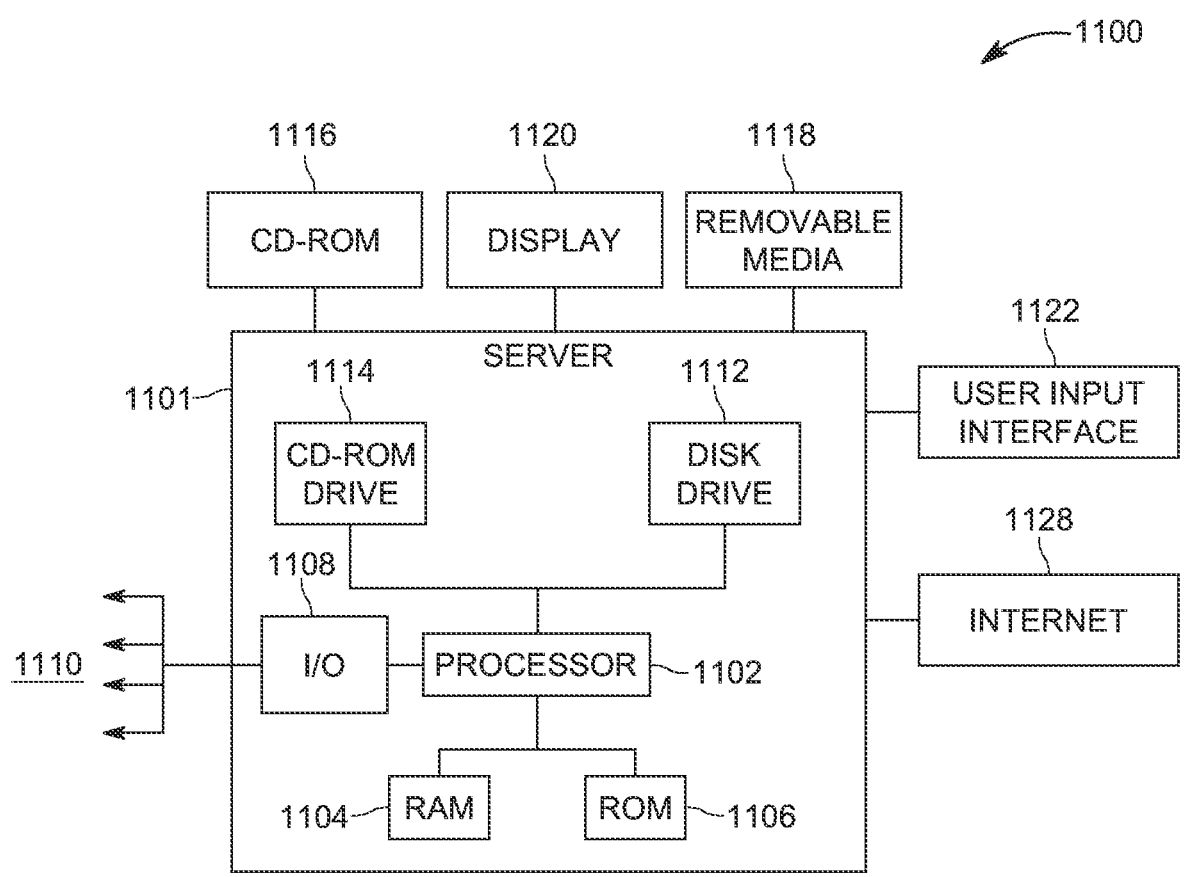
FIG. 11 illustrates a control system associated with the airborne organic matter detection system.

The above-discussed procedures and methods may be implemented in a computing device as illustrated in FIG. 11. Hardware, firmware, software or a combination thereof may be used to perform the various steps and operations described herein. The computing device 1100 may be implemented in the control center 110 or it may be the actual control center.

Computing device 1100 suitable for performing the activities described in the exemplary embodiments may include a server 1101. Such a server 1101 may include a central processor (CPU) 1102 coupled to a random access memory (RAM) 1104 and to a read-only memory (ROM) 1106. ROM 1106 may also be other types of storage media to store programs, such as programmable ROM (PROM), erasable PROM (EPROM), etc. Processor 1102 may communicate with other internal and external components through input/output (I/O) circuitry 1108 and bussing 1110 to provide control signals and the like. Processor 1102 carries out a variety of functions as are known in the art, as dictated by software and/or firmware instructions.

Server 1101 may also include one or more data storage devices, including hard drives 1112, CD-ROM drives 1114 and other hardware capable of reading and/or storing information, such as DVD, etc. In one embodiment, software for carrying out the above-discussed steps may be stored and distributed on a CD-ROM or DVD 1116, a USB storage device 1118 or other form of media capable of portably storing information. These storage media may be inserted into, and read by, devices such as CD-ROM drive 1114, disk drive 1112, etc. Server 1101 may be coupled to a display 1120, which may be any type of known display or presentation screen, such as LCD, plasma display, cathode ray tube (CRT), etc. A user input interface 1122 is provided, including one or more user interface mechanisms such as a mouse, keyboard, microphone, touchpad, touch screen, voice-recognition system, etc.

Server 1101 may be coupled to other devices, such as sources, detectors, etc. The server may be part of a larger network configuration as in a global area network (GAN) such as the Internet 1128, which allows ultimate connection to various landline and/or mobile computing devices.

The disclosed embodiments provide an efficient dynamic viral aerosol detection system that is suitable for organic matter detection at mass gatherings. The proposed system can be applied to various central public transportation systems, such as railways and airports. Also, it can be used at large events of any kind. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] Z. Xu, F. Shen, X. Li, Y. Wu, Q. Chen, X. Jie, and M. Yao, "Molecular and microscopic analysis of bacteria and viruses in exhaled breath collected using a simple impaction and condensing method," PloS one, vol. 7, no. 7, p. e41137, 2012.

[2] P. Fabian, J. J. McDevitt, W. H. DeHaan, R. O. Fung, B. J. Cowling, K. H. Chan, G. M. Leung, and D. K. Milton, "Influenza virus in human exhaled breath: an observational study," PloS one, vol. 3, no. 7, p. e2691, 2008.

[3] Z. Xu, F. Shen, X. Li, Y. Wu, Q. Chen, X. Jie, and M. Yao, "Molecular and microscopic analysis of bacteria and viruses in exhaled breath collected using a simple impaction and condensing method," PLOS ONE, vol. 7, no. 7, pp. 1-8, 072012. [Online]. Available: https://doi.org/10.1371/journal.pone.0041137

[4] W. Miekisch, J. K. Schubert, and G. Noldge-Schomburg, "Diagnostic potential of breath analysis-focus on volatile organic compounds." Clinica chimica acts; international journal of clinical chemistry, vol. 3471-2, pp. 25-39, 2004.

[5] F. Shen, M. Tan, Z. Wang, M. Yao, Z. Xu, Y. Wu, J. Wang, X. Guo, and T. Zhu, "Integrating silicon nanowire field effect transistor, microfluidics and air sampling techniques for real-time monitoring biological aerosols," Environmental science & technology, vol. 45, no. 17, pp. 7473-7480, 2011.

[6] K.-T. e. a. Park, "Detection of airborne viruses using electro-aerodynamic deposition and a field-effect transistor," Scientific Reports 5, 2015.

[7] L. Ladhani, G. Pardon, H. Meeuws, L. van Wesenbeeck, K. Schmidt, L. Stuyver, and W. van der Wijngaart, "Sampling and detection of airborne influenza virus towards point-of-care applications," PLOS ONE, vol. 12, no. 3, pp. 1-15, 032017. [Online]. Available: https://doi.org/10.1371/journal.pone.0174314

[8] J. W. Tang, A. D. Nicolle, C. A. Klettner, J. Pantelic, L. Wang, A. B. Suhaimi, A. Y. Tan, G. W. Ong, R. Su, C. Sekhar et al., "Airflow dynamics of human jets: sneezing and breathing-potential sources of infectious aerosols," PLoS One, vol. 8, no. 4, p. e59970, 2013.

[9] R. W. Bohannon, "Comfortable and maximum walking speed of adults aged 2079 years: reference values and determinants," Age and ageing, vol. 26, no. 1, pp. 15-19, 1997.

[10] S. P. Arya et al., Air pollution meteorology and dispersion. Oxford University Press New York, 1999, vol. 6.

[11] Saylan Y, Erdem Ö, Ünal S, Denizli A. An Alternative Medical Diagnosis Method: Biosensors for Virus Detection. Biosensors. 2019 June; 9(2):65.

[12] see www.flir.com/products/ibac-2/.

[13] see www.atitest.com/products/polaron-f10-real-time-bioaerosol-sensor/.

What is claimed is:

1. An aerosol detection system for detecting airborne organic matter, the detection system comprising:
   a corridor extending along a longitudinal axis and having first and second ends;
   an access gate connected to the first end of the corridor and configured to control access of an individual to the corridor;
   a person detection system located in the corridor and configured to determine the presence of the individual inside the corridor;
   a testing set configured to generate an air puff, which directs an exhaled breath of the individual for determining a presence of the airborne organic matter; and
   a controller configured to (1) activate the testing set to generate the air puff when the person detection system determines the individual is at a first distance upstream from the testing set, and (2) deactivate the testing set to stop generating the air puff when the individual is at a second distance upstream from the testing set, which is smaller than the first distance,
   wherein the corridor has a width $w_c$ that allows movement of a single individual past the testing set.

2. The aerosol detection system of claim 1, wherein the corridor has opposite first and second walls, and the testing set includes an air puffer attached to the first wall and a detection set attached to the second wall.

3. The aerosol detection system of claim 2, wherein the person detection system is located between the access gate and the testing set, and includes an infrared transmitter and an infrared sensor.

4. The aerosol detection system of claim 3, further comprising:
   a control center in communication with the access gate, the testing set, and the person detection system,
   wherein the control center is configured to control the access gate to allow entry of a single individual in the corridor at given times.

5. The aerosol detection system of claim 3, wherein the air puffer has a slot having a length $\ell_p$ and a width $w_p$, and the detection set has a length $\ell_d$, between $\ell_p$ and $1.2\,\ell_p$, and a width $w_d$, between $w_p$ and $1.2w_p$.

6. The aerosol detection system of claim 5, wherein the air puffer is configured to generate an airflow jet with a speed $u_z$, which is oriented toward the detection set, and the detection set includes plural sensors.

7. The aerosol detection system of claim 6, wherein the air puffer is configured to generate the airflow jet for a given sampling time $t_s$.

8. The aerosol detection system of claim 7, wherein the air puffer generates the airflow jet with the speed $u_z$, which is selected based on the corridor width $w_c$, the sampling time $t_s$, and an actual exhaled breath $\tilde{\ell}_z$, which is a distance in front of the individual, perpendicular on the longitudinal axis of the corridor.

9. The aerosol detection system of claim 1, wherein the testing set includes plural air puffers distributed at a distance D from each other along the longitudinal axis, and the distance D is between two times and four times the width $w_c$ of the corridor.

10. The aerosol detection system of claim 9, wherein the testing set includes plural detection sets, disposed opposite to the air puffers, and configured to include plural sensors for determining the presence of the airborne organic matter.

11. The aerosol detection system of claim 10, wherein the exhaled breath of the individual is received by the plural sensors and analyzed for the presence of the airborne organic matter.

12. A method for detecting airborne organic matter, the method comprising:
   directing an individual, through an access gate, to a corridor extending along a longitudinal axis;
   detecting a presence of the individual with a person detection system located in the corridor;
   initiating a testing set to generate an air puff when the presence of the individual is detected at a first distance upstream from the testing set, which directs an exhaled breath of the individual, to a detection set, for determining a presence of the airborne organic matter;
   stop generating the air puff when the individual is at a second distance upstream from the testing set, which is smaller than the first distance; and
   analyzing with the detection set the airborne organic matter,
   wherein the corridor has a width $w_c$ that allows movement of a single individual past the testing set.

13. The method of claim 12, wherein the corridor has opposite first and second walls, and the testing set includes an air puffer attached to the first wall and the detection set is attached to the second wall.

14. The method of claim 13, wherein the person detection system is located between the access gate and the testing set, and includes an infrared transmitter and an infrared sensor.

15. The method of claim 14, further comprising:
   controlling with a control center the access gate to allow entry of a single individual into the corridor.

16. The method of claim 14, wherein the air puffer has a slot having a length $\ell_p$ and a width $w_p$, and the detection set has a length $\ell_d$, between $\ell_p$ and $1.2\,\ell_p$, and a width $w_d$, between $w_p$ and $1.2w_p$.

17. The method of claim 16, further comprising:
   generating an airflow jet with the air puffer to have a speed $u_z$, which is oriented toward the detection set, and the detection set includes plural sensors.

18. The method of claim 17, further comprising:
   generating the airflow jet for a given sampling time $t_s$, and having a speed $u_z$, which is selected based on the corridor width $w_c$, the sampling time $t_s$, and an actual exhaled breath $\tilde{\ell}_z$, which is a distance in front of the individual, perpendicular on the longitudinal axis of the corridor.

19. The method of claim 12, wherein the testing set includes plural air puffers distributed at a distance D from each other along the longitudinal axis, and the distance D is between two times and four times the width of the corridor, and the testing set includes plural detection sets, disposed opposite to the air puffers, and the testing sets are configured to include plural sensors for determining the presence of the airborne organic matter.

20. An aerosol detection system for detecting airborne organic matter, the detection system comprising:
- a person detection system located in a corridor and configured to determine a presence of an individual passing through the corridor; and
- a testing set configured to generate an air puff, which directs an exhaled breath of the individual to a sensor for determining a presence of the airborne organic matter, wherein the testing set generates the air puff for a given sampling time $t_s$, and wherein a speed $u_z$ of the air puff is selected based on the corridor width $w_c$, the sampling time $t_s$, and an actual exhaled breath $\tilde{\ell}_z$, which is a distance in front of the individual, perpendicular on a longitudinal axis of the corridor.

* * * * *